_(12)_ United States Patent
Milanovich et al.

US007601002B2

(10) Patent No.: US 7,601,002 B2
(45) Date of Patent: Oct. 13, 2009

(54) DENTAL WHITENING METHOD

(75) Inventors: Nebojsa Milanovich, Somerset, NJ (US); Ryan B. Cameron, Somerset, NJ (US); John P. Curtis, Alpha, NJ (US); Ravi Subramanyam, Belle Mead, NJ (US); Michael Prencipe, West Windsor, NJ (US)

(73) Assignee: Colgate-Palmolive Co, New York, NY (US)

( * ) Notice: Subject to any disclaimer, the term of this patent is extended or adjusted under 35 U.S.C. 154(b) by 384 days.

(21) Appl. No.: 10/811,724

(22) Filed: Mar. 29, 2004

(65) Prior Publication Data

US 2005/0214720 A1    Sep. 29, 2005

(51) Int. Cl.
*A61C 5/00* (2006.01)
(52) U.S. Cl. ...................................... 433/215
(58) Field of Classification Search ................ 433/215, 433/216; 424/53; 206/63.5
See application file for complete search history.

(56) References Cited

U.S. PATENT DOCUMENTS

| | | | |
|---|---|---|---|
| 4,592,487 A | | 6/1986 | Simon et al. |
| 5,240,415 A | * | 8/1993 | Haynie ................ 433/216 |
| 5,252,312 A | | 10/1993 | Gentile et al. |
| 5,611,690 A | * | 3/1997 | Summers et al. ........... 433/215 |
| 5,648,064 A | * | 7/1997 | Gaffar et al. .................. 424/53 |
| 5,776,435 A | | 7/1998 | Gaffar et al. .................. 424/49 |
| 5,928,628 A | | 7/1999 | Pellico ........................ 424/49 |
| 5,965,110 A | | 10/1999 | Arnold |
| 6,149,895 A | * | 11/2000 | Kutsch ......................... 424/53 |
| 6,174,516 B1 | | 1/2001 | Curtis et al. .................. 424/53 |
| 6,365,134 B1 | | 4/2002 | Orlowski et al. |
| 6,517,350 B2 | * | 2/2003 | Diasti et al. ................. 433/215 |
| 6,576,227 B1 | * | 6/2003 | Montgomery ................ 424/50 |
| 2001/0021374 A1 | | 9/2001 | Montgomery |
| 2002/0141949 A1 | | 10/2002 | Banerjee et al. ............... 424/53 |
| 2003/0103913 A1 | | 6/2003 | Nathoo |
| 2003/0215403 A1 | | 11/2003 | Joiner et al. |

FOREIGN PATENT DOCUMENTS

| | | |
|---|---|---|
| EP | 0 897 714 | 1/2004 |
| WO | WO 96/02624 | 2/1996 |
| WO | WO 2005/041911 | 5/2005 |

OTHER PUBLICATIONS

Browning, W.D.; Use of Shade Guides for Color Measurement in Tooth-Bleaching Studies; *Journal of Esthetic and Restorative Dentistry*, vol. 15 (1), 513-520 (2003).
Rice, D.E. et al.; Laboratory Stain Removal and Abrasion Characteristics of a Dentifrice Based Upon a Novel Silica Technology; *The Journal of Clinical Denistry*, vol. XII (2), 34-37 (2001).
Stookey, G.K. et al.; In vitro Removal of Stain with Dentifrices; *Journal of Dental Research*, 61(11), 1236-1239 (1982).

* cited by examiner

*Primary Examiner*—John J Wilson
(74) *Attorney, Agent, or Firm*—Donald L. Traut

(57) ABSTRACT

A method for whitening a dental surface comprises nonsimultaneously applying a whitening composition to the surface, the whitening composition comprising at least one orally acceptable peroxy compound, and directing a volume of up to about 2.5 ml of an atomized activating composition on to the surface, wherein the activating composition comprises, in the volume so directed, a peroxy compound activating effective amount of at least one orally acceptable basifying agent, and wherein applying the whitening composition and directing the activating composition are separated by an interval not greater than a peroxy compound activating effective interval. The atomized composition can be directed on to the dental surface before or after application of the whitening composition.

15 Claims, No Drawings

DENTAL WHITENING METHOD

FIELD

This invention relates to a method for care of a dental surface, more particularly to a method for whitening a dental surface.

BACKGROUND

Effectiveness of a peroxy compound in whitening a dental surface can be enhanced in presence of a basifying agent, typically an alkaline compound such as a carbonate or bicarbonate salt, it being well known that release of oxygen from peroxy compounds such as hydrogen peroxide is promoted at higher pH. However, if a peroxy compound is formulated for storage in an alkaline medium, its effectiveness as a whitening agent can be reduced through premature release of oxygen.

Efforts to deliver to a dental surface a peroxy compound and a basifying agent to activate the peroxy compound have included simultaneous delivery of such agents in two-component products wherein the agents are kept separate until introduction to the mouth or shortly prior thereto.

For example, European Patent No. 0 897 714 discloses a two-component mouthwash product wherein one component comprises hydrogen peroxide in aqueous solution at pH<4.5 and the other a buffer salt in aqueous or aqueous/alcoholic solution at pH>8. The two components are mixed before use.

U.S. Pat. No. 5,928,628 to Pellico discloses a two-component bleaching system adapted for application to teeth from a dental bleaching tray. One component comprises a peroxide gel having a pH of about 4 to about 7 and the other an alkaline gel having a pH of about 9 to about 13. The two components are mixed before use.

U.S. Patent Application Publication No. 2002/0141949 of Banerjee & Friedman proposes applying a gel comprising a peroxide bleaching agent to a tooth surface using an applicator such as a brush having an activator (e.g., sodium carbonate or sodium bicarbonate) in a dry form stored therein.

In contrast to the above disclosures, U.S. Pat. No. 6,174,516 to Curtis et al. discloses a sequential treatment method, according to which there is first applied to teeth an aqueous rinse composition having an alkaline pH and thereafter the teeth are brushed with a peroxide dentifrice.

Patents and publications cited above are incorporated herein by reference.

There remains in the art a need for alternative methods for improving dental whitening activity of a peroxy compound by interaction thereof with a basifying agent.

SUMMARY

Now provided is a method for whitening a dental surface, the method comprising nonsimultaneously applying a whitening composition to the surface, the whitening composition comprising at least one orally acceptable peroxy compound, and directing a volume of up to about 2.5 ml of an atomized activating composition on to the surface, wherein the activating composition comprises, in the volume so directed, a peroxy compound activating effective amount of at least one orally acceptable basifying agent, and wherein applying the whitening composition and directing the activating composition are separated by an interval not greater than a peroxy compound activating effective interval.

In one embodiment, the atomized composition is applied as a pre-treatment, before application of the whitening composition.

In another embodiment, the atomized composition is applied as a post-treatment, after application of the whitening composition.

Optionally, an atomized activating composition as described above can be directed on to the dental surface both before and after application of the whitening composition; in such a method the activating composition used in the pre-treatment can be the same as or different from the activating composition used in the post-treatment.

There is further provided a kit useful in practice of such a method, the kit comprising a whitening composition that comprises at least one orally acceptable peroxy compound, and an atomizable activating composition that comprises, in a volume not greater than about 2.5 ml, a peroxy compound activating effective amount of at least one orally acceptable basifying agent.

DETAILED DESCRIPTION

A "dental surface" herein is a surface of a natural tooth or a hard surface of artificial dentition including a crown, cap, filling, bridge, denture, dental implant and the like.

The term "nonsimultaneously" herein means sequentially in either order, i.e., directing the atomized activating composition on to a dental surface can precede or follow applying the whitening composition to the surface.

The term "directing" herein means applying a composition in such a way that the composition is specifically, selectively or preferentially deposited on a targeted surface, in this case the dental surface desired to be whitened. "Directing" herein is distinguished from rinsing, as with a mouthwash composition, in which oral surfaces generally, as opposed to a targeted dental surface specifically, selectively or preferentially, are contacted by the composition.

The term "atomized" herein means in a form of discrete particles or droplets carried in a gaseous stream (typically air with or without a propellant) from an atomizing means such as a sprayer or nebulizer. The discrete particles or droplets can form, for example, a spray, an aerosol, a cloud or a mist. The particles can be solid but in most embodiments are liquid droplets, for example comprising water as a medium or diluent. Particle or droplet size is not critical, but should be such that relatively uniform deposition of the composition on the target surface is achievable. An "atomizable" composition is one that is capable of becoming atomized when dispensed from an atomizing means.

A "basifying agent" herein is an agent that raises pH in the immediate environment of a dental surface to which it is applied. The pH can be, but is not necessarily, raised to a value of about 7 or higher from an initially acidic pH level.

"Effectiveness" of an oral care agent, for example a whitening agent, herein includes one or more of (a) degree of effectiveness achieved, (b) speed with which a given degree of effectiveness is achieved and (c) duration of effect (a property sometimes referred to as "substantivity"). Effectiveness can be measured in absolute terms or in relative terms, for example by comparison with an untreated control or a standard treatment.

A "peroxy compound activating effective amount" of a basifying agent herein is an amount sufficient to enhance whitening of a dental surface by a peroxy compound such that the peroxy compound exhibits greater or faster whitening efficacy with than without the basifying agent, as determinable by in vitro or in vivo testing. Such amount is dependent on the area of the surface on to which the atomized activating composition is directed, and accordingly is most conveniently expressed as a concentration of the basifying agent in the activating composition. For example, where the basifying agent is an alkali metal carbonate or bicarbonate salt, a concentration of about 0.5% to about 20% by weight will generally be found suitable. Where a relatively high volume (e.g., about 1 ml to about 2.5 ml) of the atomized composition is directed on to the dental surface, a relatively low concentration of basifying agent can suffice, but where a lower volume (e.g., about 25 µl to about 250 µl) is used, a relatively high concentration of basifying agent will sometimes be found necessary or desirable.

A "peroxy compound activating effective interval" between applying the whitening composition and directing the atomized activating composition on to a dental surface is a period of time sufficiently short that the peroxy compound (supplied by the whitening composition) and the basifying agent (supplied by the activating composition) are coactive on the surface. "Coactive" in this context means that pH in the immediate environment of the dental surface is raised by the basifying agent during a time that the peroxy compound is available on the surface to be activated thereby. If the interval is too long in the case of pre-treatment with the activating composition, pH can return to a more acidic level not conducive to enhanced whitening efficacy of the peroxy compound, by the time the whitening composition is applied. If the interval is too long in the case of post-treatment with the activating composition, the peroxy compound can dissipate or become inactivated by the time the activating composition is applied.

An "orally acceptable" compound, composition or vehicle is one that is not harmful to a mammal in amounts disclosed herein when retained in the mouth, without swallowing, for a period sufficient to permit application to a dental surface as required herein. In general, such a compound, composition or vehicle is not harmful even if unintentionally swallowed.

The method of the invention can be seen to comprise at least two steps that can be implemented nonsimultaneously in either order. In one of the at least two steps, a whitening composition is applied to a dental surface. In another of the at least two steps, an atomized activating composition is applied to the dental surface.

The whitening composition can be, for example, a mouthwash, a dentifrice, an oral strip, a liquid whitener or a chewing gum. Dentifrices include without limitation toothpastes, gels and powders. A "liquid whitener" herein encompasses semi-liquid compositions such as gels as well as flowable liquids, so long as the composition is capable of application to a dental surface by painting with a brush or other suitable device. "Painting" in the present context means application of a thin layer of the composition to the dental surface, as is directed, for example, on the packaging of Colgate® Simply White® Night clear whitening gel sold by Colgate-Palmolive Co., New York, N.Y.

Classification herein of an ingredient as an active or a carrier ingredient is made for clarity and convenience, and no inference should be drawn that a particular ingredient necessarily functions in the composition in accordance with its classification herein. Furthermore, a particular ingredient can serve a plurality of functions, thus disclosure of an ingredient herein as exemplifying one functional class does not exclude the possibility that it can also exemplify another functional class.

Among useful oral care actives are those addressing, without limitation, appearance and structural changes to teeth, treatment and prevention of plaque, calculus, dental caries, cavities, abscesses, inflamed and/or bleeding gums, gingivitis, oral infective and/or inflammatory conditions in general, tooth sensitivity, halitosis and the like. Thus, a whitening composition useful in the method and kit of the invention can contain, in addition to at least one peroxy compound, one or more actives such as non-peroxy whitening agents, abrasives, anticalculus (tartar control) agents, fluoride ion sources, stannous ion sources, zinc ion sources, antimicrobial agents, antioxidants, sialagogue s, breath freshening agents, antiplaque agents, anti-inflammatory agents, desensitizing agents, periodontal agents, analgesics and nutrients.

Actives useful herein are normally present in a composition in amounts selected to be safe and effective. A "safe and effective" amount in the present context is an amount sufficient to provide a desired benefit, for example a therapeutic, prophylactic or cosmetic effect, when the composition is used repeatedly as described herein, without undue side effects such as toxicity, irritation or allergic reaction, commensurate with a reasonable benefit/risk ratio. Such a safe and effective amount will usually, but not necessarily, fall within ranges approved by appropriate regulatory agencies. A safe and effective amount in a specific case depends on many factors, including the particular benefit desired or condition being treated or sought to be prevented, the particular subject using, or being administered, the composition, the frequency and duration of use, etc.

Among useful carriers are diluents, pH modifying agents, surfactants, foam modulators, stabilizing agents for particular oral care actives including peroxide stabilizers, thickening agents, viscosity modifiers, mouth feel modifying agents, humectants, sweeteners, flavorants and colorants. One carrier material, or more than one carrier material of the same or different classes, can optionally be present.

The whitening composition comprises as a whitening agent at least one peroxy compound, optionally together with one or more additional whitening agents such as chlorine dioxide, chlorites and hypochlorites (e.g., chlorites and hypochlorites of alkali and alkaline earth metals such as lithium, potassium, sodium, magnesium, calcium and barium). Suitable peroxy compounds include hydrogen peroxide, peroxides of alkali and alkaline earth metals, organic peroxy compounds and peroxy acids and salts thereof. Any orally acceptable compound that delivers a perhydroxy (OOH$^-$) ion is useful. A peroxy compound can optionally be present in a form of a polymer-peroxide complex, for example a polyvinylpyrrolidone-hydrogen peroxide complex.

Peroxides of alkali and alkaline earth metals include lithium peroxide, potassium peroxide, sodium peroxide, magnesium peroxide, calcium peroxide and barium peroxide.

Organic peroxy compounds include, for example, carbamide peroxide (also known as urea hydrogen peroxide), glyceryl hydrogen peroxide, alkyl hydrogen peroxides, dialkyl peroxides, alkyl peroxy acids, peroxy esters, diacyl peroxides, benzoyl peroxide, monoperoxyphthalate and the like.

Peroxy acids and their salts include organic peroxy acids such as alkyl peroxy acids and monoperoxyphthalate, as well as inorganic peroxy acid salts including persulfate, dipersulfate, percarbonate, perphosphate, perborate and persilicate salts of alkali and alkaline earth metals such as lithium, potassium, sodium, magnesium, calcium and barium. Another useful peroxy compound is sodium pyrophosphate peroxyhydrate.

The whitening agent is present in the whitening composition in a total amount effective to result in whitening of a dental surface when applied in accordance with the disclosure herein. Peroxy compounds can illustratively be present in a total hydrogen peroxide equivalent amount of about 0.1% to about 10%, for example about 1% to about 5%, by weight of the composition.

The activating composition comprising at least one basifying agent is directed on to the dental surface in atomized form. In a kit of the invention, there is therefore provided an atomizable activating composition comprising at least one basifying agent.

In one embodiment the activating composition is a liquid comprising the at least one basifying agent in aqueous solution. According to the method of the invention, the activating composition is directed on to the dental surface in a volume not greater than about 2.5 ml. Larger volumes, such as are typically used for example when rinsing, can result in an excessive amount of the basifying agent not being retained on the target surface, thereby reducing effectiveness of the treatment. According to various embodiments, the volume of the activating composition directed on to the dental surface is about 10 µl to about 2.5 ml, or about 10 µl to about 1 ml, or about 25 µl to about 500 µl, or about 50 µl to about 250 µl.

Application of an activating composition as herein described by directed spraying on to a dental surface has been found to be surprisingly effective in enhancing speed and/or magnitude of whitening provided by a concomitantly applied whitening composition. Even more surprisingly, the effectiveness of the activating composition can be comparable whether it is applied as a pre- or post-treatment in accordance with the method of the invention.

Pre-treatment with an activating composition in the form of a rinse as described in above-cited U.S. Pat. No. 6,174,516 can be very effective but results in an excess of liquid that has to be eliminated from the mouth prior to application of the whitening composition. By contrast, the low volumes enabled by directing the activating composition in atomized form on to the particular surface desired to be whitened do not result in such an excess of liquid.

Furthermore, the rinse method of above-cited U.S. Pat. No. 6,174,516 is not readily adaptable to post-treatment, as the excess liquid provided can wash a substantial portion of the previously applied whitening agent off the dental surface. Such a drawback is not seen in the practice of the present method, which allows for maximum adherence or retention of the whitening agent on the dental surface and thereby for maximum whitening efficacy.

The interval I between a pre-treatment with an atomized activating composition and application of the whitening composition, or between application of the whitening composition and a post-treatment with an atomized activating composition, is not greater than a peroxy compound activating effective interval as defined hereinabove. Generally but not necessarily the interval I is not greater than about 1 hour, for example about 1 second to about 1 hour, or about 5 seconds to about 30 minutes, or about 10 seconds to about 10 minutes. In one embodiment the whitening composition is applied as soon as conveniently practicable after a pre-treatment as described herein. In another embodiment a post-treatment as described herein is carried out as soon as conveniently practicable after application of the whitening composition. Directing the atomizable activating composition can occur substantially immediately, for example within about 5 minutes or within about 1 minute, before or after applying the whitening composition.

Any orally acceptable alkaline substance is illustratively suitable as a basifying agent. In one embodiment the at least one basifying agent is a carbonate or bicarbonate salt of an alkali metal, for example sodium carbonate or sodium bicarbonate. In another embodiment the at least one basifying agent is an alkali metal or alkaline earth metal hydroxide, for example calcium hydroxide or sodium hydroxide.

Illustratively, where the basifying agent is sodium bicarbonate, the activating composition can comprise sodium bicarbonate at a concentration of about 0.5% to about 20%, for example about 1% to about 15% or about 2% to about 7%, by weight. Where a different basifying agent is selected, suitable concentrations are those equivalent in basifying effect to the sodium bicarbonate concentrations given above. More than one basifying agent can optionally be present. The composition can optionally be buffered.

An aqueous activating composition useful herein typically has a pH of about 8 to about 12, for example about 8.5 to about 11, or about 9 to about 10.

Optional additional ingredients that can be present in the activating composition include those detailed hereinbelow. In a particular embodiment the activating composition comprises, in addition to at least one basifying agent and water as a solvent, at least one ingredient selected from cosolvents (e.g., ethanol, propylene glycol), mouth feel modifying agents (e.g., glycerin), surfactants (e.g., poloxamers, polysorbate 80), preservatives (e.g., sodium benzoate), sweeteners (e.g., sodium saccharin), flavorants and colorants.

Basifying agents can have an unpleasant taste. For example, sodium bicarbonate has a strong salty taste. For this reason, it will generally be found desirable to include at least one sweetener and/or at least one flavorant in the activating composition. Suitable flavorants include without limitation vanillin, sage, marjoram, parsley oil, spearmint oil, cinnamon oil, oil of wintergreen (methyl salicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants and the like. Also encompassed within flavorants herein are ingredients that provide fragrance and/or other sensory effect in the mouth, including cooling or warming effects. Such ingredients illustratively include menthol, menthyl acetate, menthyl lactate, camphor, eucalyptus oil, eucalyptol, anethole, eugenol, cassia, oxanone, α-irisone, propenyl guaiethol, thymol, linalool, benzaldehyde, cinnamaldehyde, N-ethyl-p-menthan-3-carboxamide, N,2,3-trimethyl-2-isopropylbutanamide, 3-1-menthoxypropane-1,2-diol, cinnamaldehyde glycerol acetal (CGA), menthone glycerol acetal (MGA), capsicum, benzyl nicotinate and the like.

In one embodiment the whitening composition and/or the activating composition comprises a source of fluoride ions, such as a fluoride, monofluorophosphate or fluorosilicate salt. Any such salt that is orally acceptable can be used, including without limitation alkali metal (e.g., potassium, sodium), ammonium, stannous and indium salts and the like. Water-soluble fluoride-releasing salts are typically used. One or more fluoride-releasing salts are optionally present in an amount providing a total of about 100 to about 20,000 ppm, about 200 to about 5,000 ppm, or about 500 to about 2,500 ppm, fluoride ions. Where sodium fluoride is the sole fluoride-releasing salt present, illustratively an amount of about 0.01% to about 5%, about 0.05% to about 1% or about 0.1% to about 0.5%, sodium fluoride by weight can be present in the composition.

The whitening composition can optionally comprise at least one abrasive, useful for example as a cleaning and/or polishing agent. Any orally acceptable abrasive can be used, but type, fineness (particle size) and amount of abrasive should be selected so that tooth enamel is not excessively abraded in normal use of the composition. Suitable abrasives include without limitation silica, for example in the form of silica gel, hydrated silica, pyrogenic silica or precipitated silica, alumina, for example in the form of hydrated alumina or calcined alumina, aluminum silicate, bentonite, insoluble phosphates, calcium carbonate, resinous abrasives such as urea-formaldehyde condensation products and the like. Among insoluble phosphates useful as abrasives are orthophosphates, polymetaphosphates and pyrophosphates. Illustrative examples are dicalcium orthophosphate dihydrate, calcium pyrophosphate, β-calcium pyrophosphate, tricalcium phosphate, calcium polymetaphosphate and insoluble sodium polymetaphosphate. One or more abrasives are optionally present in the composition in an abrasive effective total amount, typically about 5% to about 70%, for example about 10% to about 50% or about 15% to about 30% by weight. Average particle size of an abrasive, if present, is generally about 0.1 to about 30 μm, for example about 1 to about 20 μm or about 5 to about 15 μm.

Among the above abrasives, siliceous and/or aluminous abrasives including silica, hydrated silica, pyrogenic silica, silica gels and precipitates, alumina, hydrated alumina, calcined alumina, aluminum silicate and bentonite, when used in abrasive effective amounts, are typically incompatible with peroxy compounds, in large measure because of transition metal impurities that can be present in mineral products such as these. Such incompatible abrasives, if used in the whitening composition, should therefore be segregated from the peroxy compound, for example in a dual-component composition dispensable from a dual-chamber tube or pump dispenser. Abrasives such as insoluble phosphates that are not incompatible with peroxy compounds can, if desired, be included without segregation in the whitening composition.

In a particular embodiment one or more siliceous and/or aluminous abrasives, for example hydrated silica, are present in a total amount of about 15% to about 30% by weight of the composition.

The composition can optionally include a first abrasive selected primarily for high cleaning efficacy and a second abrasive selected primarily for polishing efficacy and/or enhanced mouth feel. Such first and second abrasives are herein termed "high-cleaning" and "prophy" abrasives respectively. For example, a high-cleaning silica and a prophy silica can be included, each illustratively in a total amount of about 5% to about 15% by weight of the composition.

The whitening composition and/or the activating composition can optionally comprise at least one antimicrobial (e.g., antibacterial) agent. Any orally acceptable antimicrobial agent can be used, including without limitation triclosan (5-chloro-2-(2,4-dichlorophenoxy)phenol), 2,2'-dihydroxy-5,5'-dibromodiphenyl ether, 8-hydroxyquinoline and salts thereof, copper (II) compounds such as copper (II) chloride, fluoride, sulfate and hydroxide, zinc ion sources such as zinc citrate, zinc sulfate, zinc glycinate and sodium zinc citrate, phthalic acid and salts thereof such as magnesium monopotassium phthalate, hexetidine, octenidine, sanguinarine, benzalkonium chloride, salicylanilide, domiphen bromide, alkylpyridinium chlorides such as cetylpyridinium chloride (CPC) (including combinations of CPC with zinc and/or enzymes), tetradecylpyridinium chloride and N-tetradecyl-4-ethylpyridinium chloride, octenidine, iodine, sulfonamides, bisbiguanides such as alexidine, chlorhexidine and chlorhexidine digluconate, phenolics, piperidino derivatives such as delmopinol and octapinol, magnolia extract, grapeseed extract, phenol, thymol, eugenol, menthol, geraniol, carvacrol, citral, eucalyptol, catechol, 4-allylcatechol, hexyl resorcinol, halogenated bisphenolics such as 2,2'-methylene bis(4-chloro-6-bromophenol), methyl salicylate, antibiotics such as augmentin, amoxicillin, tetracycline, doxycycline, minocycline, metronidazole, neomycin, kanamycin and clindamycin, and the like. A further illustrative list of useful antibacterial agents is provided in U.S. Pat. No. 5,776,435 to Gaffar et al., incorporated herein by reference. One or more antimicrobial agents are optionally present in an antimicrobial effective total amount, typically about 0.05% to about 3%, for example about 0.1% to about 1% by weight, of the composition.

Among antimicrobial agents, nonionic agents such as halogenated diphenylethers (e.g., triclosan and 2,2'-dihydroxy-5,5'-dibromodiphenyl ether) and phenolic compounds are typically incompatible with peroxy compounds and should therefore be segregated from the peroxy compound if used in the whitening composition.

The whitening composition and/or the activating composition can optionally comprise at least one anticalculus agent. Any orally acceptable anticalculus agent can be used, including without limitation phosphates and polyphosphates (for example pyrophosphates), polyaminopropanesulfonic acid (AMPS), zinc citrate trihydrate, polypeptides such as polyaspartic and polyglutamic acids, polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and salts of any of these agents, for example their alkali metal and ammonium salts. Useful inorganic phosphate and polyphosphate salts illustratively include monobasic, dibasic and tribasic sodium phosphates, sodium tripolyphosphate, tetrapolyphosphate, mono-, di-, tri- and tetrasodium pyrophosphates, disodium dihydrogen pyrophosphate, sodium trimetaphosphate, sodium hexametaphosphate and the like, wherein sodium can optionally be replaced by potassium or ammonium. Other useful anticalculus agents include polycarboxylate polymers and polyvinyl methyl ether/maleic anhydride (PVME/MA) copolymers, such as those available under the Gantrez™ brand from ISP, Wayne, N.J. One or more anticalculus agents are optionally present in the composition in an anticalculus effective total amount, typically about 0.01% to about 50%, for example about 0.05% to about 25% or about 0.1% to about 15% by weight.

In a particular embodiment one or more PVME/MA copolymers are present in a total amount of about 0.3% to about 3% by weight of the composition, optionally together with one or more polyphosphate salts, e.g., tetrasodium pyrophosphate, tetrapotassium pyrophosphate, sodium tripolyphosphate and/or potassium tripolyphosphate, in a total amount of about 1% to about 15% by weight.

The whitening composition and/or the activating composition can optionally comprise at least one stannous ion source useful, for example, in helping reduce gingivitis, plaque, calculus, caries or sensitivity. Any orally acceptable stannous ion source can be used, including without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10%, for example about 0.1% to about 7% or about 1% to about 5% by weight of the composition.

The composition can optionally comprise at least one zinc ion source useful, for example, as an antimicrobial, anticalculus or breath-freshening agent. Any orally acceptable zinc ion source can be used, including without limitation zinc citrate, zinc sulfate, zinc glycinate, sodium zinc citrate and the like. One or more zinc ion sources are optionally and illustratively present in a total amount of about 0.05% to about 3%, for example about 0.1% to about 1%, by weight of the composition.

The whitening composition and/or the activating composition can optionally comprise at least one antioxidant. Any orally acceptable antioxidant can be used, including without limitation butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin and the like. One or more antioxidants are optionally present in an antioxidant effective total amount. In a particular embodiment at least one of BHA and BHT is present in the composition in a total amount of about 0.01% to about 0.1% by weight.

The whitening composition and/or the activating composition can optionally comprise a sialagogue (saliva stimulating agent), useful for example in amelioration of dry mouth. Any orally acceptable sialagogue can be used, including without limitation food acids such as citric, lactic, malic, succinic, ascorbic, adipic, fumaric and tartaric acids. One or more sialagogues are optionally present in the composition in a saliva stimulating effective total amount.

The whitening composition and/or the activating composition can optionally comprise a breath freshening agent. Any orally acceptable breath freshening agent can be used, including without limitation zinc salts such as zinc gluconate, zinc citrate and zinc chlorite, α-ionone and the like. One or more breath freshening agents are optionally present in the composition in a breath freshening effective total amount.

The whitening composition and/or the activating composition can optionally comprise an antiplaque, including plaque disrupting, agent. Any orally acceptable antiplaque agent can be used, including without limitation stannous, copper, magnesium and strontium salts, dimethicone copolyols such as cetyl dimethicone copolyol, papain, glucoamylase, glucose oxidase, urea, calcium lactate, calcium glycerophosphate, strontium polyacrylates and chelating agents such as citric and tartaric acids and alkali metal salts thereof. One or more antiplaque agents are optionally present in the composition in an antiplaque effective total amount.

The whitening composition and/or the activating composition can optionally comprise at least one anti-inflammatory agent. Any orally acceptable anti-inflammatory agent can be used, including without limitation steroidal agents such as flucinolone and hydrocortisone, and nonsteroidal agents (NSAIDs) such as ketorolac, flurbiprofen, ibuprofen, naproxen, indomethacin, diclofenac, etodolac, indomethacin, sulindac, tolmetin, ketoprofen, fenoprofen, piroxicam, nabumetone, aspirin, diflunisal, meclofenamate, mefenamic acid, oxyphenbutazone and phenylbutazone. One or more anti-inflammatory agents are optionally present in the composition in an anti-inflammatory effective amount.

The whitening composition and/or the activating composition can optionally comprise at least one desensitizing agent. Potassium salts such as potassium citrate, potassium tartrate, potassium chloride, potassium sulfate and potassium nitrate are illustratively useful in this regard, as is sodium nitrate. Alternatively or in addition a local or systemic analgesic such as aspirin, codeine, acetaminophen, sodium salicylate or triethanolamine salicylate can be used. One or more densitizing agents and/or analgesics are optionally present in the composition in a desensitizing and/or analgesic effective amount.

The whitening composition and/or the activating composition can optionally comprise at least one nutrient. Suitable nutrients include vitamins, minerals and amino acids.

The whitening composition and/or the activating composition can optionally comprise at least one thickening agent, useful for example to impart a desired consistency and/or mouth feel to the composition. Thickening agents include organic, clay-based and colloidal silica thickening agents. Any orally acceptable organic thickening agent can be used, including without limitation carbomers, also known as carboxyvinyl polymers, for example those sold under the Carbopol™ brand including Carbopols 934, 956, 974 and 980, polyvinylpyrrolidone, carrageenans, also known as Irish moss and more particularly t-carrageenan (iota-carrageenan), cellulosic polymers such as hydroxyethylcellulose, hydroxypropylmethylcellulose, carboxymethylcellulose (CMC) and carboxymethyl-hydroxyethylcellulose and salts thereof, e.g., CMC sodium, starches, and natural gums such as karaya, xanthan, gum arabic and tragacanth. Any orally acceptable clay-based thickening agent can be used, including such agents comprising natural, modified and/or synthetic clays. Illustratively, thickening agents comprising at least one clay of the smectite class, including beidellite, bentonite, hectorite, montmorillonite, saponite and stevensite, and synthetic counterparts such as colloidal magnesium aluminum silicate and Laponite™ are useful. Hydrophobically modified clays such as hydrophobically modified bentonite are also useful. One or more thickening agents are optionally present in a total amount of about 0.01% to about 15%, for example about 0.1% to about 10% or about 0.2% to about 5% by weight of the composition.

The whitening composition and/or the activating composition can optionally comprise at least one viscosity modifier, useful for example to inhibit settling or separation of ingredients or to promote redispersibility upon agitation of a liquid composition. Any orally acceptable viscosity modifier can be used, including without limitation mineral oil, petrolatum, clays and organomodified clays, silica and the like. One or more viscosity modifiers are optionally present in a total amount of about 0.01% to about 10%, for example about 0.1% to about 5% by weight of the composition.

The whitening composition and/or the activating composition can optionally comprise at least one pH modifying agent (in addition to the basifying agent present in the activating composition). Such agents include acidifying agents to lower pH, additional basifying agents to raise pH and buffering agents to control pH within a desired range. Any orally acceptable pH modifying agent can be used, including without limitation carboxylic, phosphoric and sulfonic acids, acid salts (e.g., monosodium citrate, disodium citrate, monosodium malate, etc.), alkali metal hydroxides such as sodium hydroxide, carbonates such as sodium carbonate, bicarbonates, sesquicarbonates, borates, silicates, phosphates (e.g., monosodium phosphate, trisodium phosphate, pyrophosphate salts, etc.), imidazole and the like. One or more pH modifying agents are optionally present in a total amount effective to maintain the composition in a desired pH range.

The whitening composition and/or the activating composition can optionally comprise at least one surfactant, useful for example to compatibilize other ingredients and thereby provide enhanced stability, to help in cleaning the dental surface through detergency, and to provide foam upon agitation, e.g., during brushing. Any orally acceptable surfactant, including cationic, anionic, nonionic and amphoteric types, can be used.

Suitable cationic surfactants include without limitation quaternary ammonium compounds with a $C_{8-20}$ aliphatic chain such as lauryl trimethylammonium chloride, cetyl pyridinium chloride, cetyl pyridinium fluoride, cetyl trimethylammonium bromide, diisobutylphenoxyethyl-dimethylbenzylammonium chloride, cocoalkyltrimethylammonium nitrite and the like. Cationic compounds that can stain teeth, for example chlorhexidine, can be considered for use herein, bearing this disadvantage in mind.

Suitable anionic surfactants include without limitation water-soluble salts of $C_{8-20}$ alkyl sulfates, sulfonated monoglycerides of $C_{8-20}$ fatty acids, sarcosinates, taurates and the like. Illustrative examples of these and other classes include sodium lauryl sulfate, sodium coconut monoglyceride sulfonate, sodium lauryl sarcosinate, sodium lauryl isoethionate, sodium lauryl sulfoacetate, sodium laureth carboxylate, sodium dodecyl benzenesulfonate and sodium and potassium salts of lauroyl sarcosinate, myristoyl sarcosinate, palmitoyl sarcosinate, stearoyl sarcosinate and oleoyl sarcosinate.

Suitable nonionic surfactants include without limitation poloxamers, polyoxyethylene sorbitan esters, fatty alcohol ethoxylates, alkylphenol ethoxylates, tertiary amine oxides, tertiary phosphine oxides, dialkyl sulfoxides and the like.

Suitable amphoteric surfactants include without limitation derivatives of $C_{8-20}$ aliphatic secondary and tertiary amines having an anionic group such as carboxylate, sulfate, sulfonate, phosphate or phosphonate. Examples include cocoamidopropyl betaine and lauramidopropyl betaine.

One or more surfactants are optionally present in a total amount of about 0.01% to about 10%, for example about 0.05% to about 5% or about 0.1% to about 2% by weight of the composition.

The whitening composition can optionally comprise at least one foam modulator, useful for example to increase amount, thickness or stability of foam generated by the composition upon agitation, e.g., brushing. Any orally acceptable foam modulator can be used, including without limitation polyethylene glycols (PEGs), also known as polyoxyethylenes. High molecular weight PEGs are suitable, including those having an average molecular weight of about 200,000 to about 7,000,000, for example about 500,000 to about 5,000,000 or about 1,000,000 to about 2,500,000. One or more PEGs are optionally present in a total amount of about 0.1% to about 10%, for example about 0.2% to about 5% or about 0.25% to about 2% by weight of the composition.

The whitening composition and/or the activating composition can optionally comprise at least one humectant, useful for example to prevent hardening of the composition upon exposure to air, and/or to enhance mouth feel. Any orally acceptable humectant can be used, including without limitation polyhydric alcohols such as propylene glycol, butylene glycol, glycerin, sorbitol, xylitol or low molecular weight PEGs. Most humectants also function as sweeteners. One or more humectants are optionally present in a total amount of about 1% to about 80%, for example about 5% to about 65% or about 10% to about 50% by weight of the composition.

In a particular embodiment, the whitening composition is a gel that comprises glycerin in an amount of about 10% to about 60% by weight, optionally together with a low molecular weight PEG such as PEG 600 in an amount of about 2% to about 20% by weight of the composition.

In another particular embodiment, the whitening composition is a paste that comprises sorbitol in an amount of about 10% to about 50%, optionally together with glycerin in an amount of about 5% to about 25% by weight of the composition.

The whitening composition and/or the activating composition can optionally comprise at least one sweetener, useful for example to enhance taste of the composition. Any orally acceptable natural or artificial, nutritive or non-nutritive sweetener can be used, including without limitation dextrose, polydextrose, sucrose, maltose, dextrin, dried invert sugar, lactose, mannose, xylose, ribose, fructose, galactose, corn syrup (including high fructose corn syrup and corn syrup solids), partially hydrolyzed starch, hydrogenated starch hydrolysate, sorbitol, mannitol, xylitol, maltitol, isomalt, sucralose, aspartame, acesulfame, neotame, D-tryptophan, saccharin and salts thereof (e.g., sodium saccharin), thaumatin, dihydrochalcones, dipeptide-based intense sweeteners, cyclamates (e.g., sodium cyclamate) and the like. One or more sweeteners are optionally present in a total amount depending strongly on the particular sweetener(s) selected, but typically about 0.005% to about 5% by weight of the composition.

In a particular embodiment, the whitening composition and/or the activating composition comprises sodium saccharin in an amount of about 0.01% to about 1% by weight.

The whitening composition can optionally comprise at least one flavorant, useful for example to enhance taste of the composition. Any orally acceptable natural or synthetic flavorant can be used, including without limitation those listed above as optional ingredients of the activating composition. One or more flavorants are optionally present in a total amount of about 0.01% to about 5%, for example about 0.1% to about 2.5% by weight of the composition.

The whitening composition and/or the activating composition can optionally comprise at least one colorant. Colorants herein include pigments, dyes, lakes and agents imparting a particular luster or reflectivity such as pearling agents. A colorant can serve a number of functions, including for example to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including without limitation talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride and the like. One or more colorants are optionally present in a total amount of about 0.001% to about 20%, for example about 0.01% to about 10% or about 0.1% to about 5% by weight of the composition.

In a particular embodiment, the whitening composition can comprise two or more components having contrasting colors to provide a striped effect upon extrusion from a tube or other dispenser. For example, the composition can comprise a gel component containing a blue colorant and a paste component containing titanium dioxide to appear white.

A gel composition can be prepared by mixing the ingredients in any suitable mixing device. A paste composition can be prepared by the following general procedure. Water and thickening agent(s), typically together with humectant(s) and sweetening agent(s), are mixed in a suitable mixing device until a homogeneous gel phase is obtained. Into the gel phase other ingredients, such as pigment(s) and fluoride ion source(s), can be added with further mixing until homogeneous. Thereafter, abrasive(s) and/or other desired ingredients such as anticalculus agent(s), antibacterial agent(s), flavorant(s) and surfactant(s) are added and the resulting mixture is mixed at high speed, optionally under vacuum of about 20 to about 100 mm Hg, to provide a homogeneous extrudable paste.

The dental surface to be whitened by the method of the invention can be in a human or nonhuman subject, for example a nonhuman mammalian subject such as a companion animal, for example a dog or cat. In one embodiment the dental surface is a surface of one or more natural teeth, but the method is also applicable to a surface of artificial dentition, for example a crown, a cap, a filling, a bridge, a denture or a dental implant.

Practice of the method can consist of a single two-step application as described herein, or can comprise repeated such applications. In one embodiment the present method is repeated at regular intervals, for example twice or once daily, twice or once weekly, twice or once monthly, in a program or regimen conducted at home and/or in a professional or clinical setting.

Increase in whiteness of a dental surface can be observed visually, for example with the aid of color comparison charts, gauges or shade guides, e.g., as described by Browning (2003), *Journal of Esthetic Restorative Dentistry* 15 Supp. 1, S13-S20, incorporated herein by reference.

Alternatively, increase in whiteness can be measured by colorimetry, using any suitable instrument such as a Minolta Chromameter, e.g., model CR-321 (Minolta Corp., Ramsey, N.J.). The instrument can be programmed, for example, to measure Hunter Lab values or $L^*a^*b^*$ values according to the standard established by the International Committee of Illumination (CIE). The $L^*a^*b^*$ system provides a numerical representation of three-dimensional color space where $L^*$ represents a lightness axis, $a^*$ represents a red-green axis and $b^*$ represents a yellow-blue axis. The $L^*$ and $b^*$ axes are typically of greatest applicability to measurement of tooth whiteness. Increase in whiteness can be computed from differences in $L^*$, $a^*$ and $b^*$ values before and after treatment, or between untreated and treated surfaces. A useful parameter is $\Delta E^*$, calculated as the square root of the sum of the squares of differences in $L^*$, $a^*$ and $b^*$ values, using the formula:

$$\Delta E^* = [(\Delta L^*)^2 + (\Delta a^*)^2 + (\Delta b^*)^2]^{1/2}$$

A higher value of $\Delta E^*$ indicates greater increase in whiteness. In various embodiments, the method of the present invention can effect a $\Delta E^*$ of at least about 1, or at least about 3, or at least about 5.

Evaluation of effectiveness of whitening treatments of the invention can be made, for example, in clinical studies using human volunteers, or in vivo in animals, conducted according to appropriate protocols.

Suitable in vitro protocols are also available for evaluation of whitening treatments, including those described in Examples herein and in published literature. See for example Stookey et al. (1982), *Journal of Dental Research* 61(11), 1236-1239, and Rice et al. (2001), *Journal of Clinical Dentistry* 12(2), 34-37, both incorporated herein by reference.

A kit of the invention comprises a whitening composition that comprises at least one orally acceptable peroxy compound, and an atomizable activating composition that comprises, in a volume not greater than about 2.5 ml thereof, a peroxy compound activating effective amount of at least one orally acceptable basifying agent. The whitening composition, as described above, can illustratively be a mouthwash, a gel or paste dentifrice, an oral strip, a liquid whitener or a chewing gum. The whitening composition is typically supplied in suitable packaging, for example a dispensing container such as a tube or pump where the composition is a dentifrice. The activating composition is typically supplied in a dispensing container having means for atomizing the composition, for example a spray assembly or nebulizer. Contents of the container can be under pressure, as in an aerosol can, or pressurizable for example by action of a pumping mechanism. Any spray dispenser used in the personal care arts for dispensing atomizable liquids can readily be adapted for use herein. The dispensing container can be adapted for single use (i.e., containing sufficient of the activating composition only for one pre- or post-treatment as described herein), or for multiple use (i.e., containing any convenient volume of the activating composition at least sufficient for two pre- or post-treatments as described herein, for example about 5 to about 500 ml). Illustratively, a spray dispenser commercially used for delivery of breath freshening compositions has been found suitable.

The whitening and activating composition components of the kit can be packaged separately or together and can be sold individually or as a single product. Typically instructions for use of the kit according to the method of the present invention are provided.

The kit is useful for practice of the invention in a professional setting (e.g., a dentist's or dental hygienist's office or clinic) or by the user at home or while traveling. Although adapted particularly for human use, the kit can be useful for administering oral care to nonhuman animals, for example domestic pets such as dogs.

The invention can further be understood by reference to the following nonlimiting examples.

EXAMPLES

Example 1

Activating compositions A and B were prepared having the ingredients shown in Table 1. To prepare the compositions, the various ingredients were dissolved or dispersed, with agitation, in water. Order of addition of ingredients was not critical.

TABLE 1

Activating compositions A and B

| Ingredient | Weight % A | Weight % B |
| --- | --- | --- |
| sodium bicarbonate | 4.0 | 5.0 |
| sodium hydroxide |  | 1.1 |
| ethanol | 10.0 |  |
| propylene glycol |  | 10.5 |
| glycerin | 15.0 | 15.0 |
| poloxamer 407 (Pluronic ™ F-127) | 1.0 | 1.0 |
| poloxamer 338 (Pluronic ™ F-108) | 1.0 |  |
| polysorbate 80 |  | 0.6 |
| ethoxylated castor oil |  | 0.2 |
| sodium saccharin | 0.02 | 0.1 |
| flavor | 0.15 | 1.0 |
| dye | 0.0002 | 0.002 |
| sodium benzoate | 0.5 |  |
| water | q.s. | q.s. |

Example 2

Effectiveness of a commercial tooth whitener (Colgate® Simply White® gel) in whitening artificially stained bovine teeth was tested, without an activating composition or with pre- or post-treatment by spraying with an activating composition. Teeth were stained with a combination of coffee, tea, mucin, ferric chloride and a chromogenic microbe (Sarcinea lutea). The testing method of Stookey et al., op. cit., was generally followed. The activating composition in this study contained sodium bicarbonate, 5% by weight, glycerin, 20% by weight, sodium hydroxide, 3.2% by weight, and water, q.s. to 100%.

The whitener was applied, using the brush applicator supplied with the whitener, in an amount sufficient to coat the teeth (about 10 mg). The activating composition was sprayed on to the teeth using a spray applicator commercially used for a breath-freshening product. One to two sprays, each of about 88 μl volume, were applied. Spray application of the activating composition occurred immediately before or immediately after application of the whitener.

Degree of whitening was measured at various exposure times (5, 15 and 30 minutes after treatment) by comparison with untreated teeth. Separate samples of teeth were treated for each exposure time. A Minolta CR-321 chromameter was used to determine color changes using the L*a*b* system as described above, where a higher value of ΔE* indicates greater increase in whiteness. Results are presented in Table 2.

TABLE 2

Increase in whiteness of bovine teeth

| Treatment | ΔE* | | |
|---|---|---|---|
| | 5 min | 15 min | 30 min |
| Whitener, no activating composition | 3 | 7 | 8 |
| Whitener, sprayed pre-treatment with activating composition | 24 | 28 | 31 |
| Whitener, sprayed post-treatment with activating composition | 27 | 27 | 27 |

As shown in Table 2, maximum whitening was achieved after as little as 5 minutes exposure to the combination of whitener and activating composition, whether the activating composition was sprayed as a pre- or post-treatment. Furthermore, the degree of whitening achieved by the combination (whether involving pre- or post-treatment with the activating composition) far exceeded that attained with the whitener alone.

Example 3

Effectiveness of the same commercial tooth whitener as used in Example 2 was determined in a clinical study, alone or in combination with an activating composition (Composition A of Example 1), using 5 panelists per treatment regimen. Panelists were recruited having tooth color of A3 or darker according to the Vita shade guide. The activating composition was applied either as a pre-treatment by rinsing immediately before applying the whitener or, in accordance with an embodiment of the present invention, as a post-treatment by spraying immediately after applying the whitener.

The whitener was applied according to label directions for using Colgate® Simply White® gel. For the pre-treatment, the mouth was rinsed for 30 seconds with 10-15 ml of the activating composition, which was then ejected from the mouth. For the post-treatment, the activating composition was sprayed on to the teeth using a spray applicator commercially used for a breath-freshening product. Two to three sprays, each of about 88 μl volume, were applied, sufficient to cover the area coated with the whitener. Whitening treatments according to the above protocol were repeated twice daily for the duration of the study.

Degree of whitening was measured as Vita shade guide change. Results are presented in Table 3.

TABLE 3

Vita shade guide change in clinical study

| Treatment | 2 weeks | 3 weeks |
|---|---|---|
| Whitener, no activating composition | 1.80 ± 1.64 | 3.25 ± 2.63 |
| Whitener, rinsed pre-treatment with activating composition | 3.00 ± 2.74 | 3.70 ± 2.33 |
| Whitener, sprayed post-treatment with activating composition | 4.20 ± 2.39 | 4.60 ± 2.30 |

As shown in Table 3, the whitener with post-treatment spraying of the activating composition delivered both the fastest and the greatest shade guide change of the three treatments tested.

What is claimed is:

1. A method for whitening a dental surface, the method comprising nonsimultaneously applying a whitening composition to the surface, said whitening composition comprising at least one orally acceptable peroxy compound, and directing a volume of up to about 2.5 ml of an atomized activating composition on to the surface, wherein said directing of the atomized activating composition on to the dental surface follows said applying of the whitening composition to the surface, wherein the activating composition comprises, in said volume, a peroxy compound activating effective amount of at least one orally acceptable basifying agent, and wherein applying said whitening composition and directing said activating composition are separated by an interval not greater than a peroxy compound activating effective interval.

2. The method of claim 1 wherein the activating composition raises pH in the immediate environment of the dental surface to a value of at least about 7.

3. The method of claim 1 wherein applying said whitening composition and directing said activating composition are separated by an interval not greater than about 1 hour.

4. The method of claim 1 wherein said directing of the atomized activating composition substantially immediately follows said applying of the whitening composition.

5. The method of claim 1 wherein the whitening composition is selected from the group consisting of mouthwashes, dentifrices, oral strips, liquid whiteners and chewing gums.

6. The method of claim 1 wherein the at least one peroxy compound is selected from the group consisting of hydrogen peroxide, peroxides of alkali and alkaline earth metals, organic peroxy compounds, peroxy acids and salts thereof, and polymer-peroxide complexes.

7. The method of claim 1 wherein the at least one peroxy compound is hydrogen peroxide.

8. The method of claim 1 wherein the whitening composition comprises at least one peroxv compound in a total hydrogen peroxide equivalent amount of about 0.1% to about 10% by weight.

9. The method of claim 1 wherein the activating composition is directed on to the dental surface in a volume of about 25 μl to about 1 ml.

10. The method of claim 1 wherein the activating composition is a liquid comprising the basifying agent in aqueous solution.

11. The method of claim 10 wherein the at least one basifying agent is an alkali metal carbonate or bicarbonate salt.

12. The method of claim 10 wherein the at least one basifying agent is sodium bicarbonate.

13. The method of claim 12 wherein the activating composition comprises about 0.5% to about 20% by weight sodium bicarbonate.

14. The method of claim 10 wherein the activating composition has a pH of about 8 to about 12.

15. The method of claim 10 wherein the activating composition further comprises at least one ingredient selected from the group consisting of cosolvents, mouth feel modifying agents, surfactants, preservatives sweeteners, flavorants and colorants.

* * * * *